United States Patent [19]

Houston et al.

[11] Patent Number: 5,237,777
[45] Date of Patent: Aug. 24, 1993

[54] APPARATUS FOR ELIMINATING SLACK IN MOTORIZED CABLES

[75] Inventors: John C. Houston; Richard A. McBride, both of Erie, Pa.

[73] Assignee: American Sterilizer Company, Erie, Pa.

[21] Appl. No.: 848,805

[22] Filed: Mar. 10, 1992

[51] Int. Cl.$^5$ ............................................. E05F 11/00
[52] U.S. Cl. ........................................ 49/360; 49/13; 49/26; 49/506
[58] Field of Search ...................... 49/360, 26, 28, 324, 49/13, 14, 506, 322

[56] References Cited

U.S. PATENT DOCUMENTS

| | | | |
|---|---|---|---|
| 970,380 | 9/1910 | Monson | 49/360 |
| 1,358,859 | 11/1920 | Leach. | |
| 1,936,269 | 11/1933 | Schaffert et al. | 49/322 X |
| 2,007,552 | 7/1935 | Vetterlein | 189/60 |
| 2,189,974 | 2/1940 | Buford | 49/360 X |
| 2,222,151 | 11/1940 | Morgan | 268/30 |
| 2,874,422 | 2/1959 | Fentiman | 20/19 |
| 4,150,606 | 4/1979 | Nelson | 49/360 X |
| 4,304,070 | 12/1981 | Musacchia | 49/13 X |
| 4,322,913 | 4/1982 | Himmer | 49/360 X |
| 4,887,205 | 12/1989 | Chou | 49/26 X |
| 5,072,544 | 12/1991 | Breck, Jr. | 49/322 X |

Primary Examiner—Philip C. Kannan
Attorney, Agent, or Firm—Jones, Day, Reavis & Pogue

[57] ABSTRACT

An apparatus for removing the slack from motorized cables used to control doors on sterilizers and autoclaves without the need for electro-mechanical brakes or oversized gear motors. The apparatus is adapted to be used with a door systems wherein a cable having the one end thereof attached to a motorized take-up drum and the other end thereof attached to a slack removing weight is used control the opening and closing of a door. The apparatus includes a stop plate that is rigidly fastened to the sterilizer or autoclave and a corresponding stop member that is rigidly attached to the cable. The stop plate, in conjunction with the stop member, serve to restrict the movement of the cable in only one direction thus keeping the portion of cable supporting the door taut. When additional cable is unwound from the take-up drum, the slack weight causes the cable to move in a direction away from the stop plate to keep the cable taut. The present invention also affords the gear motor controlling the take-up drum with an amount of time to develop the amount of torque required to lift the door and overcome the inertia of the system. In addition, monitoring means may be added to monitor the movement of the slack weight to determine whether the door has jammed.

15 Claims, 7 Drawing Sheets

APPARATUS FOR ELIMINATING SLACK IN MOTORIZED CABLES

BACKGROUND OF THE INVENTION

1. Field of the Invention

The invention relates to apparatus for eliminating slack in driven cables and, in particular, to apparatus for eliminating slack in motorized cables for raising and lowering autoclave and sterilizer doors.

2. Description of the Invention Background

There exists a wide variety of cable assisted devices adapted to open and close doors. In particular, devices such as the one described in U.S. Pat. No. 1,358,859 employ cables and pulleys to assist in the opening and closing of doors that are heavy and cumbersome to operate. In that device, a counterweight is attached to the free end of the cable in an effort to counteract the weight of the door so that it can be lifted more easily. The counterweight also serves to remove the slack from the cable to thereby prevent the cable from tracking off the attending pulleys.

Cable assisted devices are also used to effect the opening and closing of chamber doors on autoclaves and sterilizers used in the medical industry. In those types of applications, the chamber door is usually arranged to slide vertically within corresponding guide tracks that are mounted to the open end of the chamber. The door is suspended by a cable and pulley system that controls the movement of the door relative to the end of the chamber. Typically, one end of the cable is attached to a take-up drum that is rotatably driven by a reversible gear motor; the other end of the cable is connected to a counter weight that assists the door opening process. To close the door, the motorized take-up drum is rotated to accumulate the cable thereon. This action causes the door to slide vertically upward to a closed position. The door is opened by simply reversing the rotation of the take-up drum which permits the cable to slowly unwind therefrom. The weight of the door along with the counterweight that is attached to the free end of the cable keep the cable taut as it unwinds from the drum.

The door is lowered in this manner until it reaches a fully opened position. A stop switch arranged to detect when the door has reached the open position causes the gear motor to be de-energized. However, due to the inertia of the gear motor arrangement, the take-up drum typically continues to rotate for a short time after the gear motor has been de-energized. That additional rotation permits an additional length of cable to unwind from the take-up drum causing the cable to become slackened on the attending pulleys. Often, depending upon the amount of cable slack introduced, the cable is permitted to track off the attending pulleys causing malfunction of the door drive system. This problem has heretofore been typically alleviated by employing an expensive electro-mechanical brake system to stop the rotation of the take-up drum as soon as the gear motor is de-energized by the stop switch. Thus, the need exists for a method of eliminating the cable slack without the use of expensive electrically controlled components such as electro-mechanical brakes.

Another problem typically encountered with prior cable systems is that a gear motor having high starting torque capabilities must be used. More specifically, the prior cable and gear motor arrangements cause the gear motor to encounter a load corresponding to the weight of the door and the inertia of the system immediately upon being activated. As such, a gear motor that is capable of developing the starting torque necessary to immediately overcome the weight of the door and the inertia associated with the cable controlled system must be used. It will be appreciated that gear motors having that kind of starting torque capabilities are larger and more expensive than similar gear motors having smaller starting torque capabilities. Thus, the need exists for a simple cable operated door system wherein a smaller and less expensive gear motor can be utilized.

Yet another problem commonly encountered with prior cable controlled door operating systems is the inability to automatically monitor the door's progress while it is being opened. Should the door become jammed or obstructed while it is being opened, the operator may not discover the problem until excess cable has been partially or completely unwound from the take-up drum causing damage and malfunction. As such, there is a need for a monitoring and controlling apparatus for cable-controlled doors wherein the gear motor is automatically stopped without operator intervention when the door becomes jammed while opening and wherein the operator is provided with timely notice of the problem.

SUMMARY OF THE INVENTION

In accordance with the present invention, there is provided an improved design for cable slack eliminators used to eliminate the slack in motorized cables for controlling the opening and closing of doors for autoclave or sterilizer chambers, as well as more customary cable controlled door systems. The apparatus of the present invention is adapted to be used on sterilizer and autoclave door systems wherein the door is suspended and controlled by a cable that has one end thereof connected to a motorized take-up drum while the other end thereof is connected to a means for applying force to the cable such as a slack weight or spring. However, while the unique features of the present invention are particularly adapted for use with the door system described immediately above, it will be understood that some of the features may be employed with other door operating systems using flexible members such as chains or ropes in place of the cable and other devices such as hydraulic or pneumatic cylinders in place of the motorized take-up drum.

The present cable slack eliminating apparatus includes a stop plate that is rigidly attached to the side of the sterilizer or autoclave chamber. A bore is provided through the stop plate that is adapted to freely receive the cable therein. A stop member having a girth that is larger than the diameter of the bore provided in the stop plate is attached to the cable at a location between the slack weight and the stop plate.

Accordingly, to open the door, the reversible gear motor controlling the rotation of the take-up drum is activated to cause the cable to unwind from the take-up drum. The cable is permitted to unwind from the take-up drum until the door reaches a fully open position wherein the gear motor is de-energized. Typically, upon de-activation of the gear motor, an additional length of cable is permitted to unwind from the take-up drum. However, because the cable is free to move in a direction away from the stop plate, the cable is kept taut by the slack weight. In doing so, the stop member is caused to move away from the stop plate a distance that is equivalent to the length of cable that was unwound after the door stops moving. As such, when the gear motor is re-activated, it is afforded an amount of time equivalent to the time needed to wind a length of cable onto the take-up drum that is equivalent to the length of cable extending between the stop member and stop plate before encountering the weight of the door. Thus when compared to gear motors of prior cable systems, the gear motors used with the present invention can be smaller because the torque required at start up is limited to the weight of the slack weight and not the weight of the door.

To close the door, the gear motor rotation is reversed thereby causing the cable to be wound onto the take-up drum. In doing so, the cable is permitted to pass freely through the bore in the stop plate for a short period of time wherein the door does not move and the cable tension is limited to the tension created by the slack weight. However, when the stop member contacts the stop plate, the cable end becomes fixed and the cable tension is that induced by the weight of the door. Consequently, the portion of cable extending between the stop member and the take-up drum continues to accumulate on the take-up drum thus causing the door to slide vertically upward to a closed position. Upon reaching a fully closed position, a sensor switch de-energizes the gear motor.

In yet another embodiment of the present invention, the slack weight is replaced by a coil spring. In particular, one end of the coil spring is attached to the end of the cable that is not attached to the take-up drum. The other end of the spring is then attached to a bracket extending from the chamber. It will be appreciated that when assembled in the above-described manner, the coil spring serves to apply a small force to the one end of the cable as did the slack weight in the previously described embodiment.

According to another embodiment of the present invention, a sensor switch in connection with a timer and a microprocessor may be used to provide the sterilizer operator with an alarm or warning message when the door becomes jammed while opening. In particular, the sensor switch is arranged to detect any vertical movement of the slack weight during the opening process. Analysis of the movement of the slack weight is performed to determine whether the door has jammed during the opening process or whether sensor failure has occurred. The gear motor is automatically deactivated and an appropriate alarm is initiated in response to the foregoing analysis.

Accordingly, the present invention provides solutions to the aforementioned problems encountered when using motorized cables for controlling the opening and closing of autoclave and sterilizer doors. The present invention provides a means for eliminating the slack in the motorized cable without the need for an expensive electro-mechanical brake and gear motor. In addition, the present invention provides a means for automatically monitoring the opening of the door to determine whether it has jammed and, if so, for automatically providing an alarm. These and other details, objects and advantages will become apparent as the detailed description of the present invention proceeds.

BRIEF DESCRIPTION OF THE DRAWINGS

The preferred embodiment of the invention will now be described by way of example only, with reference to the accompanying Figures wherein like members bear like reference numerals and wherein.

DETAILED DESCRIPTION OF THE PREFERRED EMBODIMENT

Referring now to the drawings which are for purposes of illustrating the preferred embodiment of the present invention only and not for purposes of limiting the same, the Figures show a cable slack eliminating device generally designated as 10, adapted to remove the slack from a cable 40 used to open and close the door 14 of a conventional sterilization chamber 12. More particularly and with reference to FIGS. 1 and 2, the sterilization chamber 12 is exemplary of typical sterilization chambers having cable-controlled doors, the construction and operation of which are well known in the art. As such, a detailed description of the sterilization chamber 12 need not be set forth herein beyond that which is necessary to understand the present invention. Also, it will be appreciated by those of ordinary skill in the art that the cable slack eliminating device of the present invention may be easily adapted to similar applications wherein it is desirable to remove the slack from motorized cables. In addition, it will be further appreciated that the present invention may be adapted to remove the slack in a variety of flexible door opening members such as, for example, ropes and chains.

Figure 1:
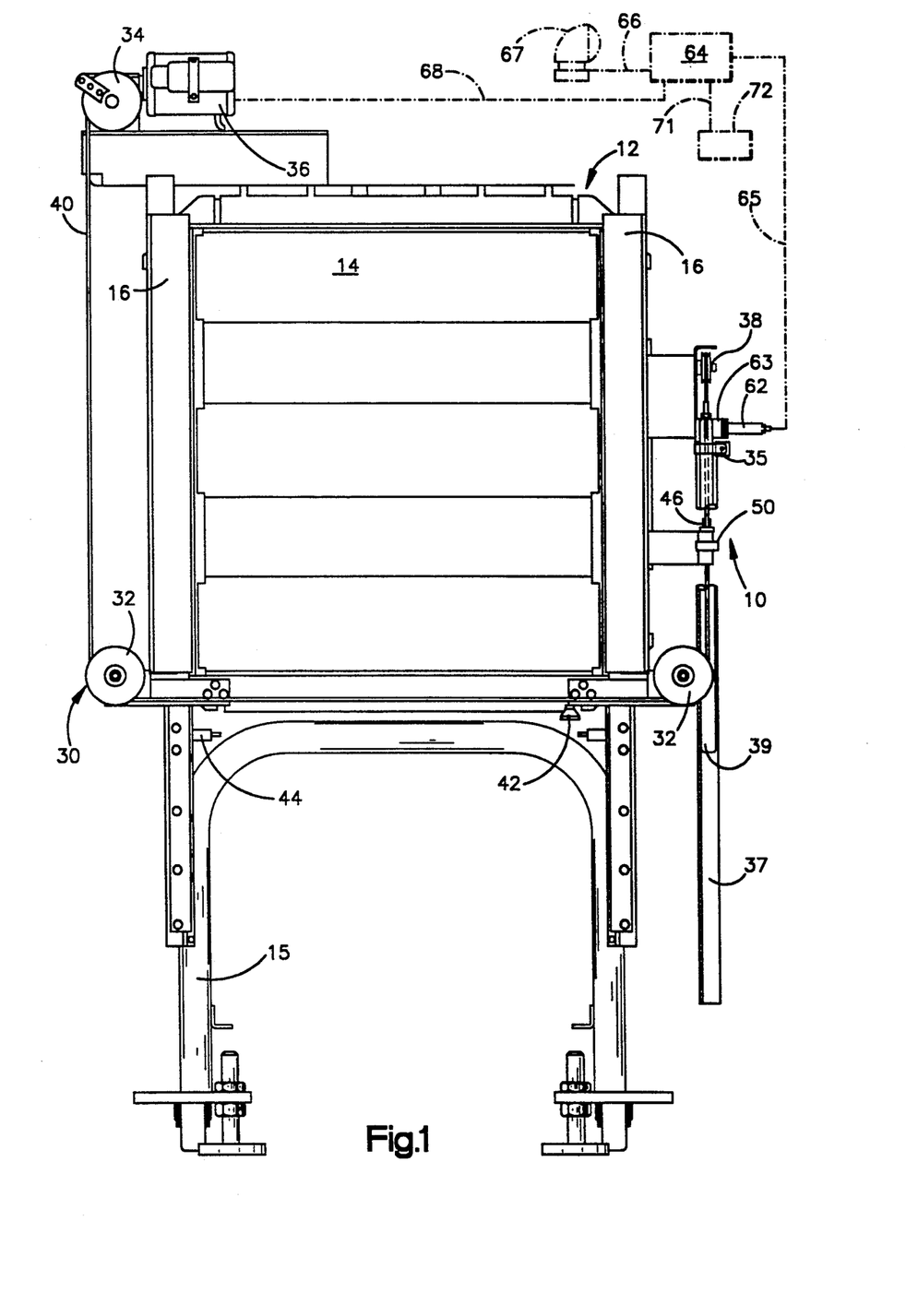
FIG. 1 is a front elevational view of the preferred embodiment of the cable slack eliminator of the present invention connected to a sterilizer door system.
Figure 2:
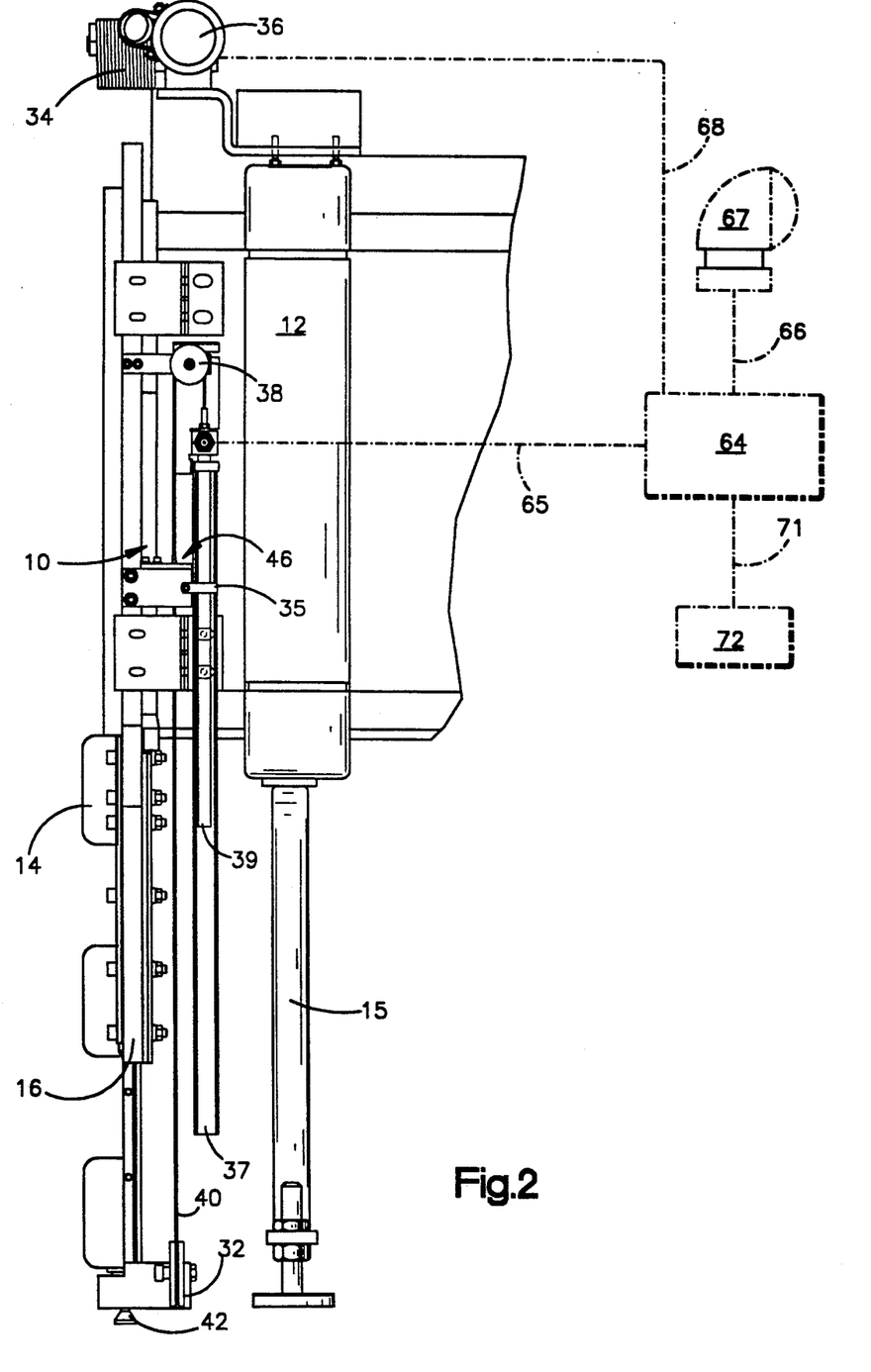
FIG. 2 is a side elevational view of the cable slack eliminator and sterilizer door system of FIG. 1.

As shown in FIGS. 1 and 2, a sterilization chamber 12 having a vertically slidable door 14 attached thereto is supported above the floor level by a stand member 15. The sterilizer door 14 is slidably attached to the open end of the sterilization chamber 12 by door retainer hardware generally designated as 16. More specifically, the door retainer hardware 16 is attached to each side of the sterilization chamber 12 and the stand member 15 to provide a vertical way system wherein the door is free to slide vertically to an open and closed position. The door 14 is moved vertically within the door retainer hardware 16 by a pulley and cable system generally designated as 30.

The pulley and cable system 30 consists of a pair of pulleys 32 that are rotatably fastened to the lower corners of the door 14 and are adapted to receive a cable 40 therein. One end of the cable 40 is attached to a take-up drum 34 that is rotatably attached to the top of the sterilization chamber 12. A reversible gear motor 36, is attached to the take-up drum 34 and supplies the rotational motion necessary to wind the cable 40 onto the take-up drum 34. The opposite end of the cable 40 is attached to a slack-removing weight 39 that is suspended over a third pulley 38 that is rotatably attached to the sterilization chamber 12. Typically, the slack weight 39 is received in a hollow member 37 that is attached to the side of the chamber 12 by clamps 35 and is adapted to restrict the lateral movement of the weight 39 as the door 14 is opened and closed.

A bottom support member 42 is normally attached to the bottom of the door 14 and is adapted to support the door above the floor when the door is in the fully opened position. It will be appreciated that the conventional gear motors generally used in these applications invariably permit the take-up drum 34 to unwind an additional length of cable 40 after the door 14 has reached the fully opened position and the gear motor 36 has been de-energized. Prior devices have utilized an expensive electro-mechanical brake (not shown) to prevent the take-up drum 34 from rotating after the door 14 has reached the fully opened position and the gear motor 36 has been de-energized.

Figure 3:
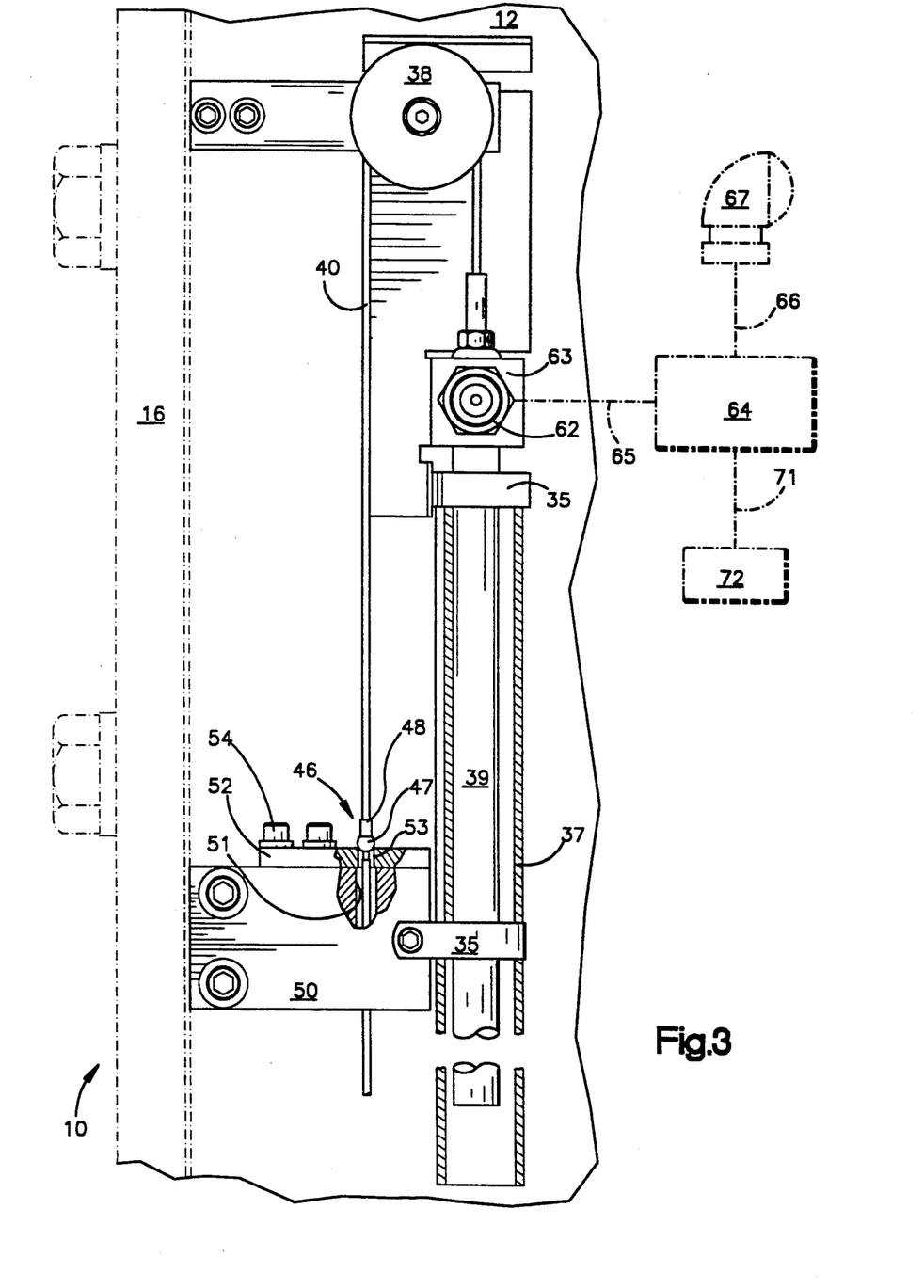
FIG. 3 is a side view of the cable slack eliminator of the present invention.

The present invention is adapted to eliminate the above-mentioned cable slack without the need for an expensive electro-mechanical brake while also enabling a smaller gear motor to be utilized. The present invention includes a stop member 46 that is fastened to the cable 40 and is adapted to engage a stop plate 52 that is attached to the side of the chamber 12 via a mounting block 50. As can be seen in FIG. 3, the cable 40 slidably extends through a bore 51 located in the mounting block 50 and a corresponding slot 53 provided in the stop plate 52.

Figure 4:
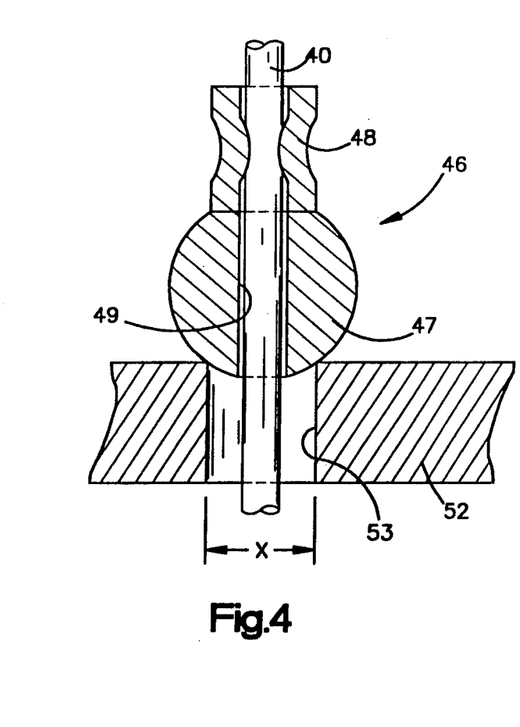
FIG. 4 is a cross-sectional view of the stop member of the present invention.

As can also be seen in FIGS. 3 and 4, the stop member 46 preferably has an upper collar portion 48 and a lower portion 47 that is greater in diameter than the width of the slot 53 located in the stop plate 52. The stop member 46 has a bore 49 extending therethrough that is adapted to slidably receive the cable 40 therein. In the preferred embodiment, as shown in FIG. 4, the stop member 46 is rigidly fastened to the cable 40 by crimping the collar portion 48 into the cable 40. It will be appreciated by those of ordinary skill in the art, however, that the stop member 46 may be rigidly attached to the cable 40 by a myriad of known clamping and fastening means. As can further be seen in FIG. 3, the stop member 46 is attached to the portion of cable 40 that extends between the third pulley 38 and the stop plate 52 when the door is in the open or down position.

To simplify the assembly process, in the preferred embodiment, the bore 51 in the mounting block 50 is greater in diameter than the lower portion 47 of the stop member 46 so that the stop member 46 may, during assembly, be inserted through the bore 51 while being attached to the cable 40. Thereafter, the stop plate 52 is then attached to the mounting block 50 via at least two cap screws 54 that are received in threaded bores (not shown) located in the mounting block 50.

When constructed in the above-described manner, the present invention enables the cable 40 to slide unobstructed through the slot 53 in the stop plate 52 and the bore 51 in the mounting block 50 while it is being wound onto the take-up drum 34. The cable 40 will continue to pass through the slot 53 and bore 51 until the stop member 46 contacts the stop plate 52 thereby causing the portion of the cable 40 extending between the stop plate 52 and the take-up drum 34 to support the weight of the door. At this time, the cable 40 is restricted to move only in a direction toward the pulley 38. As such, when the cable 40 is being wound onto the take-up drum 34, it will be held taut by the weight of the door 14 acting on the portion of cable 40 extending between the take-up drum 34 and the stop member 46. Conversely, should a small amount of cable 40 be permitted to unwind from the take-up drum 34, the slack weight 39 will immediately cause the cable 40 to remain taut by causing the cable 40 to move in a direction toward the pulley 38.

Figure 5:
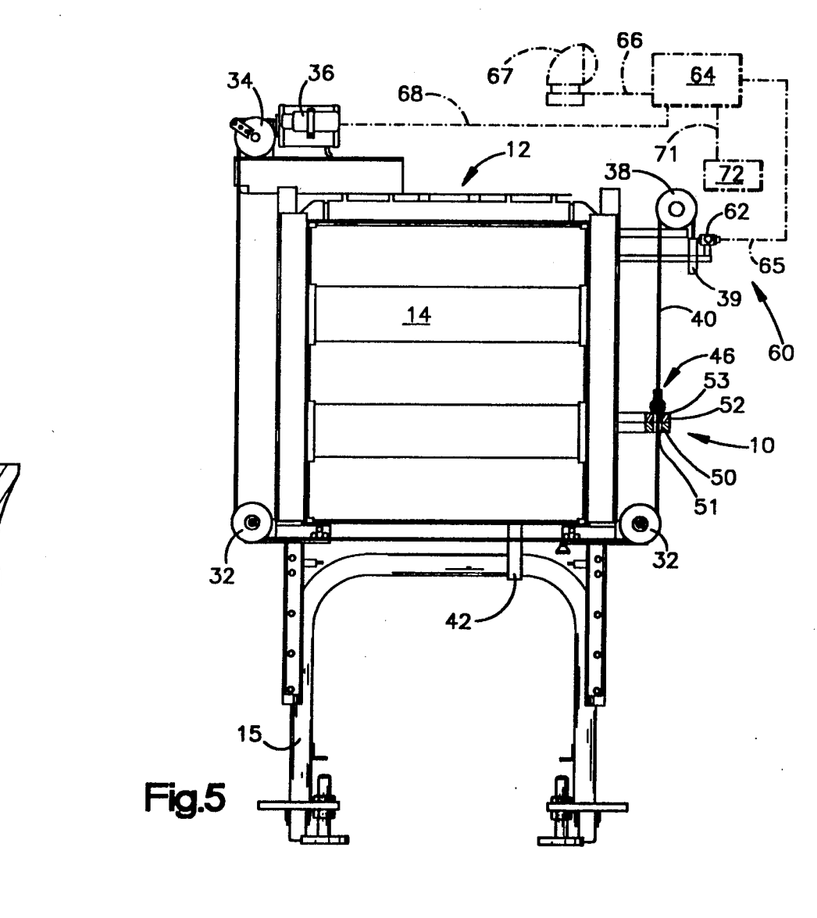
FIG. 5 is a diagrammatic view of a sterilization chamber and the cable slack eliminator of the present invention showing the sterilizer door in the closed or fully up position.

An understanding of the operation of the present invention can be gleaned from FIGS. 5–8 wherein, for purposes of clarity, the elements described immediately above are depicted in diagram form. More specifically, FIG. 5 illustrates the door 14 in the fully up or closed position. To achieve the closed position depicted in FIG. 5, the operator starts the gear motor 36 via a starting switch (not shown) which causes the cable 40 to be wound onto the take-up drum 34. Initially, the cable 40 passes freely through the slot 53 and the bore 51, respectively, in a direction towards the take-up drum 34 until the stop member 46 contacts the stop plate 52. Thereafter, the cable 40 continues to accumulate on the take-up drum 34 thus causing the door 14 to slide vertically to the closed position. A sensor switch (not shown) is strategically positioned on the sterilizer 12 to detect when the door 14 has reached the closed position. When the door has reached the closed position, the sensor switch communicates with the gear motor 36 through electrical conductors (not shown) to cause the gear motor 36 to be de-energized. As such, when in the position depicted in FIG. 5, the door is supported by the taut length of cable 40 that extends between the take-up drum 34 and the stop member 46.

Figure 6:
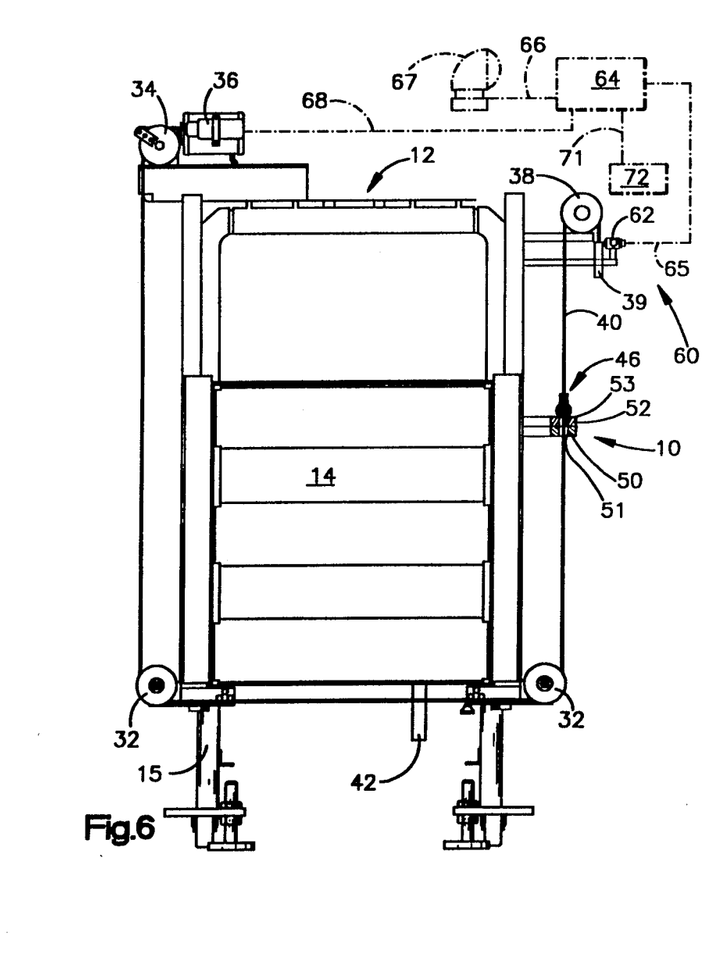
FIG. 6 is a diagrammatic view of the sterilization chamber and cable slack eliminator of FIG. 5 showing the sterilizer door in a partially closed position.
Figure 7:
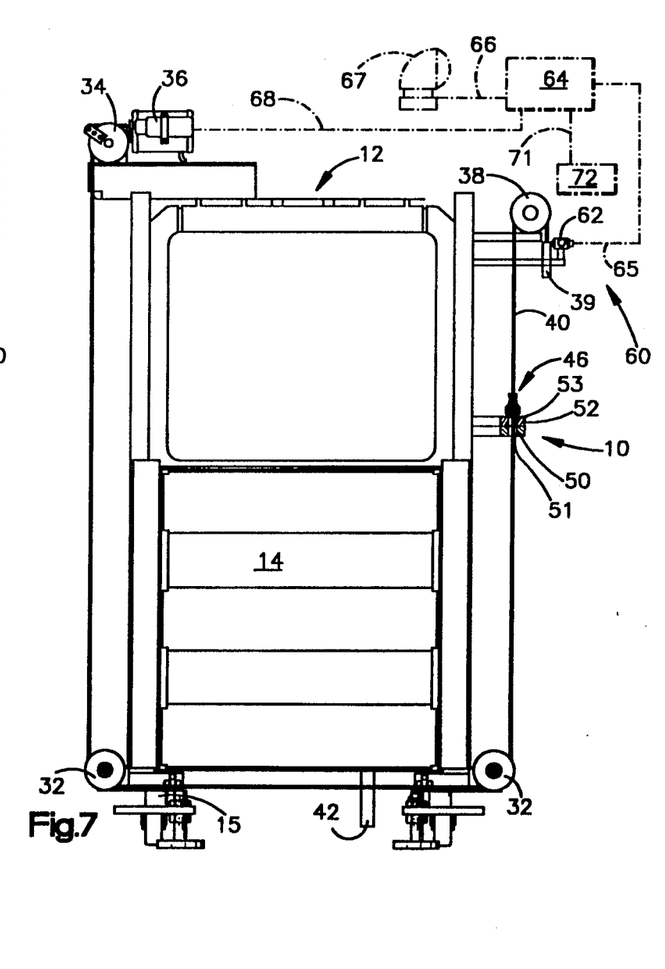
FIG. 7 is a diagrammatic view of the sterilization chamber and cable slack eliminator of FIGS. 5 and 6 showing the sterilizer door in a fully open position.

FIG. 6 depicts the door 14 in a partially opened position wherein the door 14 is also fully supported by the length of cable 40 that extends between the take-up drum 34 and the stop member 46. FIG. 7 illustrates the door 14 just as it reaches a fully opened position but immediately before the slack weight has begun to move. It will be understood that when in the fully opened position, the door 14 is supported by the support member 42 which extends between the bottom surface of the door 14 and the floor.

Figure 8:
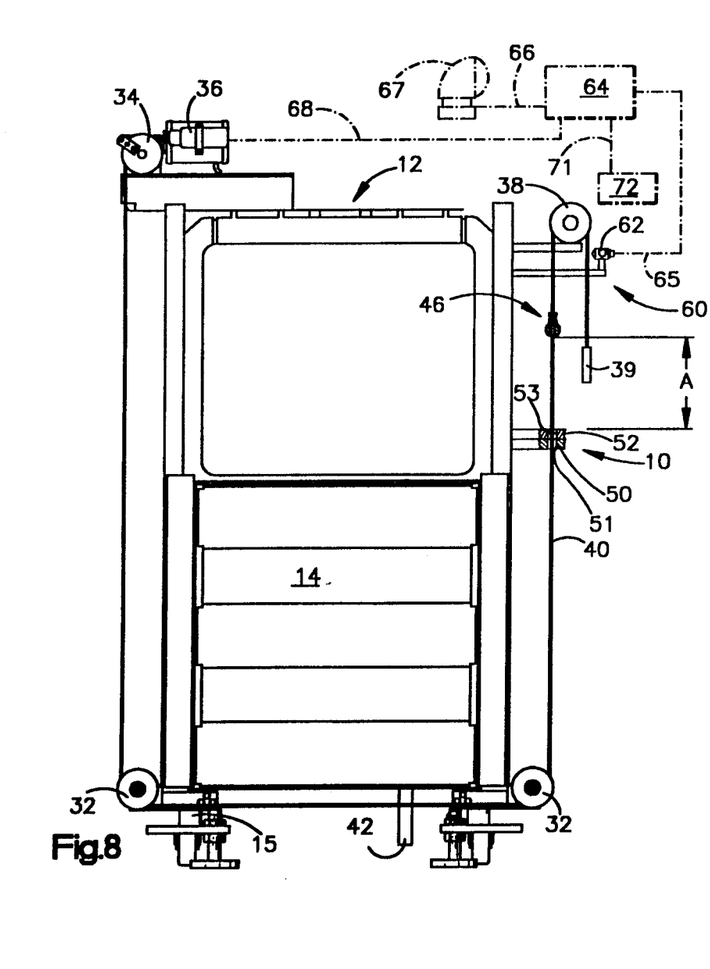
FIG. 8 is a diagrammatic view of the sterilization chamber and cable slack eliminator of FIGS. 5-7 after the door has reached the open position and an additional amount of cable has been permitted to unwind from the take-up drum.

FIG. 8 illustrates the present invention after the gear motor 34 has been de-energized and an additional length of cable, generally designated as "A", has been permitted to unwind from the take-up drum 34. It will be understood that the slack weight 39, in cooperation with the pulley 38, serves to keep the cable 40 taut when the additional length "A" of cable 40 is unwound from the take-up drum 34. When the gear motor 34 is reactivated, however, a length of cable 40, corresponding to the length designated as "A", is initially wound onto the take-up drum 34 before the stop member 46 contacts the stop plate 52. As such, the gear motor 36 does not immediately encounter the weight of the door 14 but instead is initially faced with a small load represented by the weight of the slack weight 39.

Figure 9:
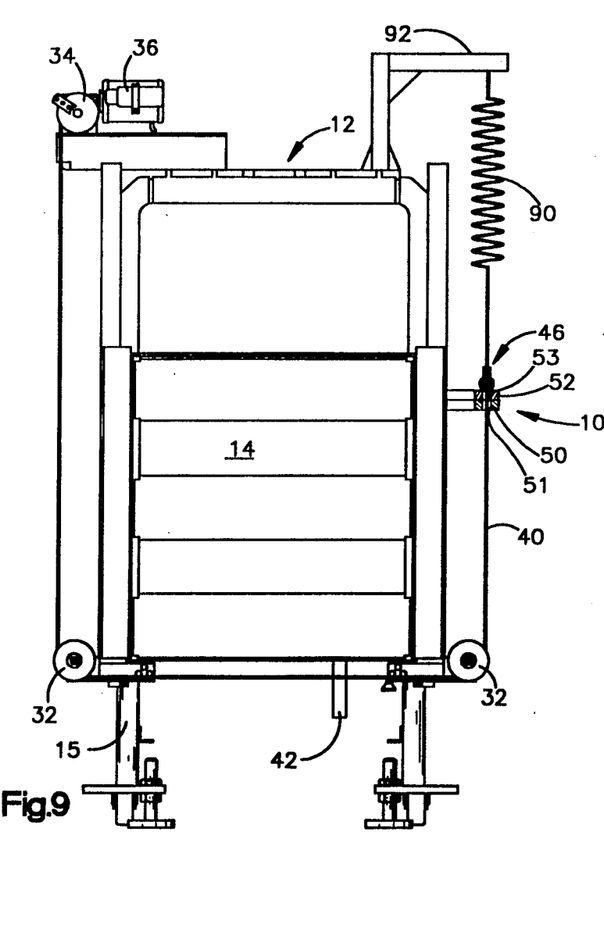
FIG. 9 is a diagrammatic view of the present invention wherein a coil spring is used to keep the cable taut.

In yet another embodiment, as illustrated in FIG. 9, a coil spring 90 is substituted for the slack weight 39. In particular, a spring member 90 having the one end thereof attached to a bracket member 92 affixed to the top of the chamber 12 is attached to the end of the cable 40 that is opposite the take-up drum 34. It will be appreciated that when assembled in the above-described manner, the coil spring serves to apply a small force to the one end of the cable as did the slack weight 39.

As can be seen in FIGS. 5-7, during normal door opening operations, the slack weight 39 remains static until the door reaches the fully opened position. However, if the door 14 becomes jammed or obstructed during the opening process, excess cable will be unwound from the drum and thus cause the slack weight to move. Therefore, in another preferred embodiment of the present invention, we employ a slack weight monitoring system, generally designated as 60, to determine whether the door 14 has jammed while being opened. More specifically, a conventional sensor switch 62 is arranged to detect the normal static position of the slack weight 39 and communicate any deviation therein to a conventional microprocessor 64 which, through its control program, determines whether the door 14 has jammed and, if so, provides the operator with an appropriate alarm signal.

The sensor 62 and the micro-processor 64 are exemplary of proximity sensing switches and microprocessors that are well-known in the art. However, those of ordinary skill in the art will recognize that other types of electro-mechanical sensor switches may be used. As such, the construction and operation of the sensor 62 and the microprocessor 64 need not be discussed herein beyond that which is necessary to fully appreciate and understand the present invention.

Figure 10:
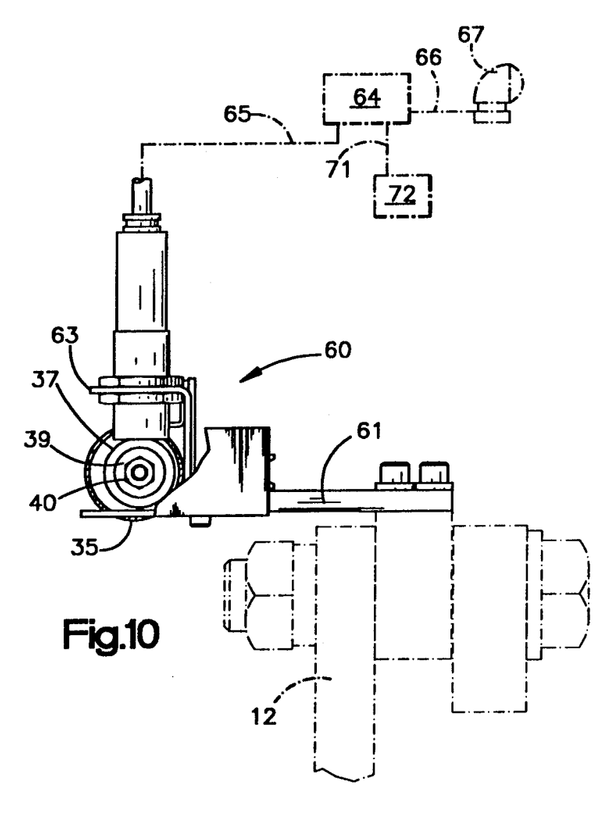
FIG. 10 is a top view of the cable and sensor arrangement of the present invention.

Referring now to FIGS. 1 and 10, sensor 62 is preferably removably attached to the side of the chamber 12 via a bracket member 63 that permits the sensor 62 to monitor the position of the slack weight 39. In the preferred embodiment, the bracket member 63 is fastened to a stand off member 61 that is preferably bolted to the side of the chamber 12. As further illustrated in FIG. 10, the sensor 62 is connected to the microprocessor 64 by control line 65. The microprocessor 64 is also connected to an alarm generating device such as, for example, a CRT 67 via a control line 66. It will be appreciated, however, that other forms of alarm generating devices such as line printers, light emitting diodes, bells and whistles may also be used. In addition, the microprocessor 64 is also capable of de-energizing the gear motor 36 through control line 68 (See FIGS. 5-8).

In this embodiment, the sensor 62, in conjunction with the micro-processor 64 and the slack weight 39, is used to de-energize the gear motor 36 after the door 14 has reached a fully down or open position. More specifically, when the support member 42 contacts the floor, thus signifying that the door 14 has reached the fully open position, the gear motor 36 continues to unwind cable 40 from the take-up drum 34. The slack weight 39 keeps the cable 40 taut by moving towards the floor. That movement of the slack weight 39 is detected by the sensor 62 which, through control line 65, communicates to the microprocessor 64. The microprocessor 64 thereafter de-energizes the gear motor 36 through the control line 68.

However, to use the proximity sensor 62 and the microprocessor 64 to their fullest advantage and to provide a method of monitoring the operation of the door 14 as it is opened via the cable and pulley system 30 of the present invention, the timing characteristics of the cable and pulley system 30 must first be determined. More specifically, the amount of time required to lower the door 14 from a fully closed position (See FIG. 5) to a fully opened position (See FIG. 7) must be determined. It will be understood that the amount of time "X" referred to above only encompasses the amount of time to elapse from starting the gear motor 36 until the bottom support member 42 that is attached to the door 14 contacts the floor. That amount of time, designated as "X" seconds, can easily be determined by lowering the door 14 and timing its progression with a stop watch. After "X" has been determined, it is entered into the control program of the microprocessor 64.

Figure 11:
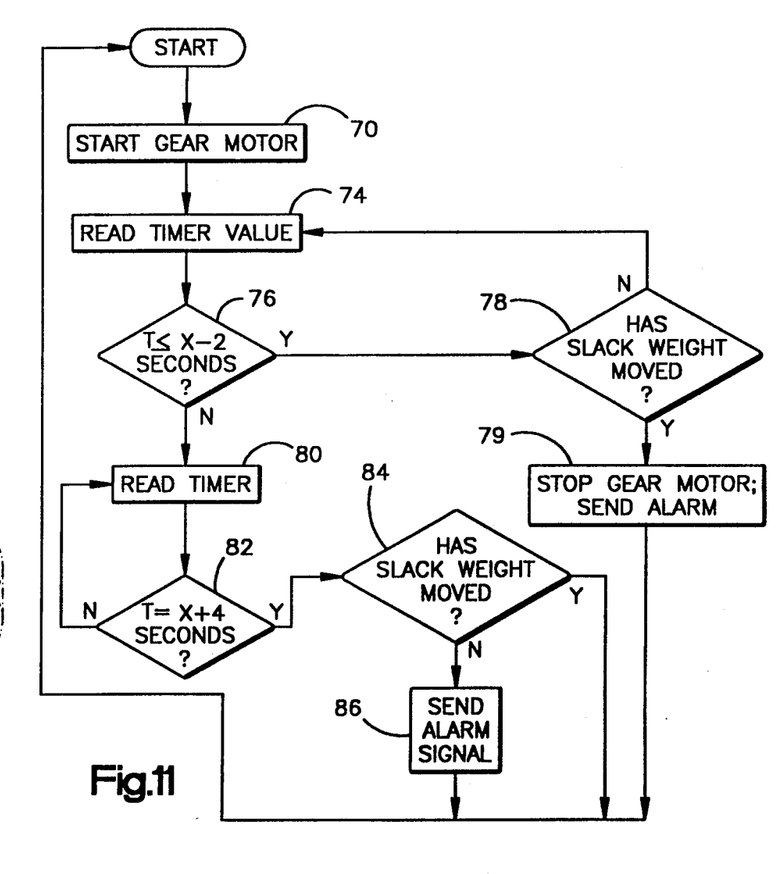
FIG. 11 is a flow chart illustrating the steps performed by the microprocessor of the door monitoring and alarm system of the present invention.

The operation of the slack weight monitoring system 30 may be implemented as illustrated in the flow chart of FIG. 11. The flow chart begins at step 70 wherein the gear motor 36 is started by an operator controlled switch (not shown). At this time, a conventional timer 72 communicating with microprocessor 64 through a control line 71 is also started to time the entire door opening process. It will be understood that "T", as referred to in FIG. 11, represents the amount of time that has accumulated on timer 72 from the time the gear motor 36 was started.

As was discussed above, after the support member 42 contacts the floor, the gear motor 36 continues to unwind the cable 40 from the take-up drum 34 thus causing the slack weight 39 to move. The sensor 62 is arranged to detect this movement of the slack weight 39 and send a signal to the microprocessor 64 to de-energize the gear motor 36. In the preferred embodiment, if the sensor 62 has not detected movement of the slack weight 39 within "X" plus four seconds, we assume that the sensor 62 has failed. It will be appreciated by those of ordinary skill in the art that the amount of time allotted in addition to the normal opening time "X" will vary from system to system depending upon other system variables such as, for example, the speed and temperature characteristics of the gear motor and the manufacturing tolerances of the various system components.

As can be seen in FIG. 11, the micro-processor 64 reads the timer value "T", through known data acquisition techniques, in step 74. The microprocessor 64 then performs an analysis to determine whether "T" is greater than "X" plus four seconds in step 76. If "T" is less than or equal to "X" plus four seconds, the control program will continue with step 78. However, if the microprocessor 64 has determined that "T" is greater than "X" plus four seconds, the control program will proceed to step 86 wherein the gear motor 36 is de-energized by the microprocessor 64 through the control line 68. The control program then proceeds to step 88 wherein the microprocessor 64 sends an appropriate alarm signal to the CRT 67 through the control line 66 indicating sensor failure.

In step 78, the microprocessor 64 performs an analysis to determine whether the sensor 62 still senses the slack weight 39. If the sensor 62 senses the presence of the slack weight 39, the control program returns to step 74. If, however, the sensor switch 62 does not detect the slack weight 39, the control program proceeds to step 80 wherein the gear motor 36 is de-energized through the control line 68. Thereafter, the control program proceeds to step 82.

It will be understood that if the door 14 should jam during the opening process, cable slack will continue to be generated as the gear motor 36 continues to unwind the cable 40 from the take-up drum 34. Consequently, the introduction of that slack causes the slack weight 39 to move in a direction towards the floor. In the preferred embodiment, if the slack weight has moved any time prior to "X" minus two seconds, the door 14 is considered to have jammed. Once again, however, it will be recognized by those of ordinary skill in the art that the "X" minus two seconds value may vary somewhat with the types of components being used and their operating characteristics.

In step 82, the microprocessor 64 performs an analysis to determine whether "T" is less than "X" minus two seconds. If "T" is greater than or equal to "X" minus two seconds, it is assumed that the door 14 has opened properly. However, if "T" is less than "X" minus two seconds, the control program will proceed to step 84 wherein the microprocessor 64 sends an appropriate alarm signal indicating a jammed door condition to the CRT 67 through control line 66.

Should the door become jammed while being opened, the sensor 62 in cooperation with the microprocessor 64 sends an alarm signal to the CRT 67 so the operator may take appropriate corrective action. In addition, the present invention also provides detection means to assure that the gear motor has been properly de-energized after the door 14 has reached the fully opened position.

The present invention addresses the various problems encountered when using prior cable and pulley systems to control doors. The instant invention also provides a method for monitoring the opening of sterilizer doors. However, it will be appreciated that various changes in the details, materials and arrangements of parts which have been herein described and illustrated in order to explain the nature of the invention, may be made by those skilled in the art within the principle and scope of the invention as expressed in the appended claims.

What is claimed is:

1. A door opening system for moving a chamber door between open and closed positions relative to a chamber opening, comprising:
   a flexible member adapted to movably support said door thereon and having a first end and second end;
   a first means for applying a first force to said first end of said flexible member which is effective for moving said door between said open and closed positions;
   means for restricting the movement in the direction of said first force only of said second end of said flexible member when said door is suspended on said flexible member; and
   a second means for applying a second force to said second end of said flexible member in the direction opposite said first force which is effective for removing slack in said flexible member wherein said second force is less than the weight of said door.

2. The door opening system of claim 1 wherein said restricting means comprises:
   a stop plate fastened to said chamber; and
   a stop member fastened to said flexible member such that said stop member engages said stop plate when said door is supported on said flexible member and whereby further movement of said flexible member in the direction of said first force applying means is prevented.

3. The door opening system of claim 2 further comprising means for detecting when said door is jammed.

4. The door opening system of claim 3 further comprising means responsive to said detecting means, said responsive means being adapted to initiate an alarm.

5. The door opening system of claim 4 wherein said means for applying a force to said second end of said flexible member comprises a weight member attached to said second end of said flexible member.

6. The door opening system of claim 5 wherein said detecting means includes means for determining whether said weight member has moved.

7. The door opening system of claim 6 further comprising means for determining whether the movement of said weight member is indicative of a jammed door condition.

8. The door opening system of claim 2 wherein said means for applying a force to said second end of said flexible member comprises a spring member having the one end thereof attached to said second end of said flexible member and the other end thereof attached to said chamber.

9. The door opening system of claim 2 wherein said flexible member comprises a cable.

10. The door opening system of claim 9 wherein said force application member comprises a motorized pulley adapted to wind said cable thereon and unwind said cable therefrom.

11. An apparatus for removing the slack from a cable used to move a chamber door between open and closed positions relative to a chamber opening, wherein the cable has a first end and a second end comprising;
   at least one first pulley rotatably attached to said door and adapted to receive said cable therein so that said door is supported on said cable;
   a rotatably motorized pulley attached to said chamber, said motorized pulley being attached to said first end of said cable and being adapted to wind and unwind the cable thereon to cause said door to move to said open and closed positions;
   a tension member attached to said second end of said cable, said tension member being adapted to apply a force to said second end of said cable in a direction tending to unwind the cable; and
   means for restricting the movement of said second end of said cable in the direction tension member to keep said cable constantly tending to wind the cable.

12. The apparatus of claim 11 wherein said restricting means comprises:
   a stop plate attached to said chamber, said stop plate being constructed so that said cable may slidably pass therethrough; and
   a stop member attached to said cable, said stop member being constructed to contact said stop plate to thereby restrict the movement of said cable in one direction.

13. The apparatus of claim 12 wherein said tension member comprises a weight member attached to said second end of said cable.

14. The apparatus of claim 13 wherein said tension member comprises a spring member having one end thereof attached to said second end of said cable and the other end thereof attached to said chamber.

15. A method for automatically monitoring the operation of a cable controlled door wherein one end of said cable is attached to a motorized cable take-up member and wherein the other end of said cable is attached to a weight comprising the steps of:

detecting the movement of said weight;
determining whether said movement of said weight is indicative of a jammed door condition; and
automatically providing an alarm action in response to said determination.

* * * * *